United States Patent [19]

Vanhoye et al.

[11] Patent Number: 5,256,748
[45] Date of Patent: Oct. 26, 1993

[54] PRECURSORS OF POLYMERS CONTAINING ISOCYANURATE UNITS

[75] Inventors: Didier Vanhoye, Forbach; Paul Grosius, Petite-Rosselle, both of France

[73] Assignee: Autochem, Paris, France

[21] Appl. No.: 722,495

[22] Filed: Jul. 2, 1991

[30] Foreign Application Priority Data

Jul. 2, 1990 [FR] France ............... 90 08316

[51] Int. Cl.$^5$ .............................................. C08F 26/08
[52] U.S. Cl. ..................................... 526/261; 544/215
[58] Field of Search .............. 526/261; 544/221, 222

[56] References Cited

U.S. PATENT DOCUMENTS 4,159,376  6/1979  Kuehn ........................... 544/222
4,485,226  11/1984  Noll et al. ....................... 528/45
4,526,920  7/1985  Sakashita et al. .................. 524/850

OTHER PUBLICATIONS

R. T. Morrison and R. N. Boyd, Organic Chemistry, 3rd Ed., Allyn & Bacon, Boston, 1973, pp. 494–497; 602–603.
J. March, "Advanced Organic Chemistry" 2nd Ed., McGraw-Hill, New York, 1977 pp. 704–706.
Chemical Abstracts, vol. 102, No. 2, Abstract No. 7116a (Jan. 14, 1985).
Chemical Abstracts, vol. 80, No. 23, Abstract No. 133489q (1974).
Kauffman et al., Journal of Polymer Science, vol. 12, No. 8, pp. 1735–1743 (1974).

Primary Examiner—Joseph L. Schofer
Assistant Examiner—Mark Nagumo
Attorney, Agent, or Firm—Millen, White, Zelano & Branigan

[57] ABSTRACT

Oligomers of the formula

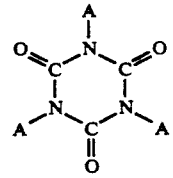

wherein:
(1) at least one $A = -CH_2CHR^1COODOH$ (a) ($R^1 = H$, $CH_3$ and $D = C_1-C_4$ alkylene), the other A's $= H$ or $C_1-C_4$ alkyl, it being possible for at least a part of the residues (a) to be converted into $A^1 = -CH_2CHR^1COODOCONHD^1NCO$ ($D^1$ = divalent organic residue), it being possible for at least a part of the residues $A^1$ to be converted into $A^2 = -CH_2CHR^1COODOCONHD^1NHCOOR^2$ ($R^2$ = monovalent radical obtained by removal of OH from a monoalcohol containing a vinylidene group);
(2) at least one $A = D^2OCONHD'^1NHCOOR'^2$ (b) where $D^2 = C_1-C_4$ alkylene or $-D^3-(-O-D^3-)_n-$, with $D^3 = C_1-C_4$ alkylene and $n = 1-12$; $D'^1$ analogous to $D^1$; $R'^2$ analogous to $R^2$; the other residue(s) A denoting $-D^2OCONHD'^1NCO$.

These oligomers are intended especially to be copolymerized under ultraviolet radiation in a reactive diluent and in the presence of an initiator so as to form (co)polymers which have good hardness and good thermal resistance and which can be employed in the field of coatings, inks, and photopolymerizable adhesives.

19 Claims, No Drawings

PRECURSORS OF POLYMERS CONTAINING ISOCYANURATE UNITS

BACKGROUND OF THE INVENTION

The present invention relates to precursors of polymers containing isocyanurate units, also comprising hydroxyl, urethane, isocyanate or acrylic functional groups and combinations of these functional groups, and to processes for their manufacture. These polymer precursors of the present invention, which are called oligomers hereinafter and which contain hydroxyl functional groups, form starting compounds for the manufacture of oligomers of the invention containing urethane, isocyanate or acrylic functional groups and combinations of these functional groups. These oligomers are intended especially to be copolymerized under ultraviolet radiation in a reactive diluent and in the presence of an initiator, so as to form (co)polymers which have good hardness and good thermal resistance, and which can be employed in the field of coatings, inks and photopolymerizable adhesives.

U.S. Pat. No. 4,159,376 discloses a process for the preparation of an ethylenically unsaturated isocyanurate which consists in reacting an aromatic polyisocyanate with a monoalcohol containing a vinylidene group, chosen especially from hydroxypropyl (meth)acrylate, hydroxyethyl (meth)acrylate and their mixtures, to form a urethane containing a monoisocyanate, and a second stage consisting in reacting the said urethane with tri(2-hydroxyethyl) isocyanurate.

U.S. Pat. No. 4,485,226 discloses a process for the manufacture of a compound which crosslinks under the effect of a high-energy radiation, containing an isocyanurate group, olefinic double bonds and, if appropriate, blocked or free isocyanate groups. This process comprises the reaction of a polyisocyanate containing an isocyanurate group with a compound containing at least one group which reacts with isocyanate groups and at least one olefinic double bond, such as a hydroxylated ester of acrylic or methacrylic acid with an aliphatic dialcohol which has a molecular mass of approximately 62–300, to form a urethane, the quantitative ratios of the reactants being chosen so that, for each free isocyanate group of the polyisocyanate, the reaction mixture contains approximately 0.9–1.5 hydroxyl groups of the other reactant.

SUMMARY OF THE INVENTION

An object of the present invention is to provide new (isocyanato)-urethano-acrylic oligomers containing isocyanurate units, and new oligomers containing isocyanurate units comprising hydroxyl groups and forming possible starting reactants for the manufacture of the above-mentioned new oligomers First of all, therefore, a subject of the invention is oligomers containing isocyanurate units, denoted by the following formula:

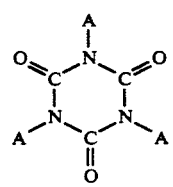

in which:
(1) at least one residue A denotes a residue

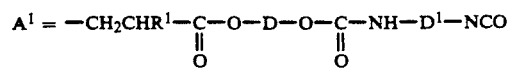

wherein
$R^1 = H$ or $CH_3$ and
$D = C_1-C_4$ alkylene residue, the other residues A denoting H or $C_1-C_4$ alkyl, it being possible for at least a part of the residues A of formula (a) to be converted into residues

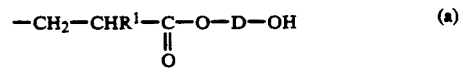

(where $D^1$ is a divalent organic radical free from groups which react with isocyanate groups and obtained by elimination of 2 NCO groups from a polyisocyanate), it being possible for at least a part of the residues $A^1$ to be converted into groups

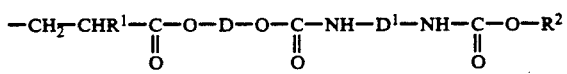

(where $R^2$ is a monovalent radical obtained by elimination of the hydroxyl group from a monoalcohol containing a vinylidene group), and mixtures of these different compounds;

(2) at least one residue A denotes a group of formula:

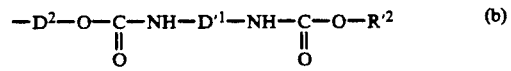

in which:
$D^2$ is a $C_1-C_4$ alkylene residue optionally substituted by halogen; or a residue $—D^3—(—O—D^3—)_n—$ where $D^3$ is a $C_1-C_4$ alkylene residue optionally substituted by halogen, and n is an integer from 1 to 12;
$D'^1$ is analogous to $D^1$ defined above;
$R'^2$ is analogous to $R^2$ defined above, the other residue(s) A denoting

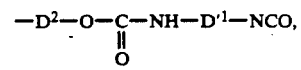

$D^2$ and $D'^1$ being as defined above, $D^2$ being incapable of denoting $CH_2—CH_2—$ in the case where the oligomer carries the three groups (b), and the mixtures of these compounds.

A particular group of these oligomers is that in which $R^2$ or $R'^2$ are denoted by:

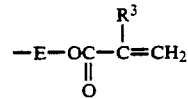

where:
R³ denotes H or CH₃; and
E denotes a unit

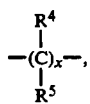

x being an integer from 1 to 12, and $R^4$ and $R^5$, which are identical or different, being chosen from the hydrogen atom and alkyl radicals containing 1 to 4 carbon atoms.

In particular the case may be cited where $R^2$ or $R'^2$ originate from at least one out of hydroxypropyl (meth)acrylate, hydroxyethyl (meth)acrylate and their mixtures.

$R^2$ or $R'^2$ can also originate from a hydroxyalkyl (meth)acrylamide.

The oligomers according to the present invention may be in a dilute state in a multifunctional acrylate, in an oligomer/multifunctional acrylate ratio of approximately 20 to 80% by weight.

A multifunctional acrylate as referred to in the present invention means, generally, products of esterification of acrylic acid or methacrylic acid with polyols such as especially trimethlolpropane oxyethyl triacrylate, diethoxyethyl bisphenol A diacrylate, trimethylolpropane trimethacrylate, hexanediol diacrylate, tripropylene glycol diacrylate, ethylglycol acrylate and ethoxylated pentaerythritol tetraacrylate.

The invention also relates to a process for the preparation of the oligomers as defined in point (1) above, characterised in that:
in a first stage a Michael reaction is carried out between a compound of formula

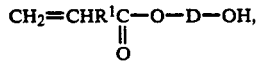

R¹ and D being as defined above, and isocyanuric acid, with basic catalysis and in a solvent medium, to obtain a mixture of oligomers which are separated, if appropriate, into individual oligomers;
if appropriate, in a second stage, a urethanisation is carried out by reacting the oligomer(s) obtained with a polyisocyanate OCN—D¹—NCO, D¹ being as defined above; and
if appropriate, in a third stage, a reaction of the product from the preceding stage is carried out with a monoalcohol R²OH, R² being as defined above;
then, if appropriate, the solvent is removed.

The Michael reaction in the first stage is conducted especially at a temperature of approximately 60° to 100° C., over a period of approximately 1 to 4 hours, and heating is then carried out at a temperature of approximately 110° to 156° C. for 0.1 to 2 hours; the catalyst is then neutralised and a purification stage is carried out.

The catalyst for the Michael reaction is especially a tertiary amine such as triethylamine, a quarternary ammonium salt, a tertiary phosphine or an alkaline base such as sodium hydroxide or sodium acetate.

The solvent is chosen from polar aprotic solvents such as dimethylformamide, N-methylpyrrolidine, ethyl acetate and acetonitrile. The final purification may consist in decolorising with active carbon, filtering and then, if appropriate, evaporating off the solvent at reduced pressure.

Any polyisocyanate may be employed in the second stage. A "polyisocyanate" means a compound containing at least two NCO groups. The polyisocyanate may be saturated, unsaturated, aromatic, aliphatic, cycloaliphatic, monomeric or polymeric. The only requirement is that the polyisocyanate should not contain any groups which would give rise to the reaction of the isocyanate group of the polyisocyanate with the hydroxyl group of the compound or mixture of compounds from the first stage. Examples of polyisocyanates which are particularly useful in the present invention include 2,4-tolylene diisocyanate, 2,6-tolylene diisocyanate, m-phenylene diisocyanate, p-phenylene diisocyanate, 1,5-naphthalene diisocyanate, 1,6-hexamethylene diisocyanate, 4,4'-diphenyl ether diisocyanate, 4,4',4"-triphenylmethane triisocyanate, 2,4,4'-triisocyanatotriphenyl, 2,4,4'-triisocyanatodiphenylmethane, 2,4,6-triisocyanatodiphenyl ether, 2,2',4-triisocyanatodiphenyl ether, 2,2',4-triisocyanatodiphenyl sulphide, 2,4,4'-triisocyanatodiphenyl sulphide, 2,3',4-triisocyanato-4'-methyldiphenyl ether, 2,3',4-triisocyanato-4'-methoxydiphenyl ether, 2,4,4'-triisocyanato-3'-chlorodiphenyl ether, 4,4',6-diphenyl triisocyanate, 1,10-decamethylene diisocyanate, cumene 2,4-diisocyanate, 4-methoxy-1,3-phenylene diisocyanate, 4-chloro-1,3-phenylene diisocyanate, 4-bromo-1,3-phenylene diisocyanate, 4-ethoxy-1,3-phenylene diisocyanate, 2,4'-diisocyanatodiphenyl ether, 5,6-dimethyl-1,3-phenylene diisocyanate, benzidine diisocyanate, 9,10-anthracene diisocyanate, 4,6-dimethyl-1,3-phenylene diisocyanate, 4,4'-diisocyanatodibenzyl, 3,3'-dimethyl-4,4'-diisocyanatodiphenylmethane, 2,6-dimethyl-4,4'-diisocyanatodiphenyl, 2,4-diisocyanatostilbene, 3,3'-dimethyl-4,4'-diisocyanatodiphenyl, 3,3'-dimethoxy-4,4'-diisocyanatodiphenyl, 1,4-anthracene diisocyanate, 2,6-fluorene diisocyanate, 1,8-naphthalene diisocyanate, 2,6-diisocyanatobenzofuran, 2,4,6-tolylene triisocyanate, 2,4,4'-triisocyanatodiphenyl ether, the diphenylmethane polyisocyanate available under the manufacturing mark Mondur MR which has a functionality of 2.6, and 1,3-xylene-4,6-diisocyanate. A preferred class of polyisocyanates consists of aromatic polyisocyanates. Preferred polyisocyanates are 2,4-tolylene diisocyanate, 2,6-tolylene diisocyanate, commercial tolylene diisocyanate (a mixture of 80% of the 2,4 isomer and 20% of the 2,6 isomer), methylene di(p-phenylisocyanate), 1,3-cyclopentylene diisocyanate, 2,4,6-toluene triisocyanate, p-xylylene diisocyanate, tetramethylene diisocyanate, hexamethylene diisocyanate, 2,2,4-trimethylhexamethylene diisocyanate, 2,4,4'-trimethylhexamethylene diisocyanate, 3-isocyanatomethyl-3,5,5-trimethylcyclohexyl diisocyanate, bis(2-isocyanatoethyl carbonate), isocyanate-ended diol and triol prepolymers, and isocyanate-ended polyester prepolymers.

The conditions of this second stage of urethanisation are the conditions which are conventional in technology for reacting an alcohol with an isocyanate to form a urethane, that is to say a temperature of approximately between 20° C. and 120° C., with possible use of catalysts such as tin octoate or dibutyltin dilaurate, and a polar aprotic solvent which does not contain any functional group capable of reacting with the isocyanate functional group.

The monoalcohols R²OH which can be used in the third stage of the abovementioned process include any monoalcohol containing a vinylidene (CH₂=C<)

group and which is free from groups, other than the hydroxyl group, which react with isocyanate groups. A preferred class of monoalcohols is prepared by reacting a monocarboxylic acid containing a vinylidene group with a dialcohol. Illustrative examples of such acids include acrylic acid, methacrylic acid, ethacrylic acid, 9,12-octadecadienoic acid, 9,12,15-octadecatrienoic acid, 9,11,13-octadecatrienoic acid and 4-keto-9,11,13-octadecatrienoic acid. Illustrative examples of dialcohols include ethylene glycol, propylene glycol, diethylene glycol, dipropylene glycol, 1,3-butylene glycol, 1,4-butylene glycol, 2,3-butylene glycol, pentamethylene glycol, hexamethylene glycol, neopentyl glycol, dibromoneopentyl glycol, dimethylhexenediol, dimethylhexanediol, 2-butene-1,4-diol, 2-butane-1,4-diol, 2,3-dibromo-2-butene-1,4-diol, 2,2,3,3-tetrachloro-1,4-butanediol, 2,2,4-trimethyl-1,6-hexanediol, 2,5-dimethyl-2,5-hexanediol, 2,2,4,4-tetramethyl-1,3-cyclobutanediol, 1,4-cyclohexanediol, 1,4-cyclohexanedimethanol, hydrogenated bisphenol A and ethylene oxide and/or propylene oxide ethers of the diols referred to above. A preferred group of monoalcohols which can be used in the process of this invention includes hydroxypropyl methacrylate, hydroxyethyl methacrylate, hydroxyethyl acrylate and hydroxypropyl acrylate and their mixtures. Furthermore, as already indicated above, the monoalcohol R²OH may consist of a hydroxyalkyl-acrylamide or a hydroxyalkyl-methacrylamide.

The reaction conditions of this third stage are generally identical with those of the second stage. Given the unsaturated nature of the monoalcohol R²OH, it is preferable, however, to operate in conditions which prevent any polymerisation, for example by bubbling dry air through and/or by operating in the presence of an effective quantity of at least one polymerisation inhibitor. As examples of polymerisation inhibitors which can be employed there may be mentioned especially phenothiazine, hydroquinone methyl ether, N,N-diethylhydroxylamine, nitrobenzene, di-tertbutylcatechol, hydroquinone, p-anilinophenol, di(2-ethylhexyl) octyphenyl phosphite, 2,5-di-tertbutyl-4-hydroxytoluene, methylene blue and their mixtures in all proportions. An effective quantity of polymerisation inhibitor is generally between 0.05% and 0.5% by weight of the polymerisable compounds.

The invention also relates to a process for the preparation of the oligomers as defined in point (2) above, in which at least one residue A denotes a group of formula

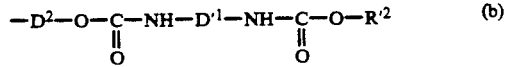 (b)

in which:
D² is a C₁-C₄ alkylene residue optionally halogen-substituted; or a residue —D³—(—O—D³—)ₙ— where D³ is a C₁-C₄ alkylene residue optionally halogen-substituted, and n is an integer from 1 to 12;
D'¹ is analogous to D¹ defined above;
R'² is analogous to R² defined above, the other residue(s) A denoting

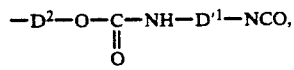

D² and D'¹ being as defined above, characterised in that:
in a first stage, a compound of formula:

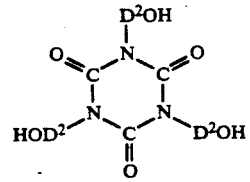

is reacted with a polyisocyanate OCN—D'¹—NCO; and
in a second stage, the compound obtained, in which all the D²OH have been replaced with

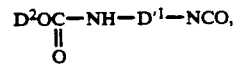

is reacted with a compound of formula R'²OH, in a molar ratio of 1 to 3 of R'²OH to the preceding compound.

The polyisocyanates and the hydroxyl compounds R'²OH are chosen from those indicated above with reference to the first process. The reaction conditions are, similarly, those of a conventional urethanisation.

At least a part of the solvent employed is advantageously a multifunctional acrylate as defined above.

Finally, the present invention relates to any polymer or copolymer including in its chain at least one unit derived from an oligomer containing an isocyanurate unit as described above. Such a copolymer may additionally contain units derived from at least one comonomer which can be copolymerised with the said oligomer, such as especially:
a multifunctional acrylate as defined above,
an alkyl acrylate or methacrylate in which the linear or branched alkyl group contains from 1 to 20 carbon atoms, and
an aryl acrylate or methacrylate such as benzyl methacrylate,
a vinylaromatic hydrocarbon such as styrene, vinyltoluene, alpha-methylstyrene, 4-methylstyrene, 3-methylstyrene, 4-methoxystyrene and 1-vinylnaphthalene.

The following examples illustrate the present invention without, however, limiting its scope. In these examples the percentages are given by weight unless indicated otherwise, and the following abbreviations have been employed:
AC: isocyanuric acid
Triton B: benzyltrimethylammonium hydroxide
TEBAC: triethylbenzylammonium chloride
HEA: hydroxyethyl acrylate
HEMA: hydroxyethyl methacrylate
HPA: hydroxypropyl acrylate
HPMA: hydroxypropyl methacrylate
HQME: hydroquinone methyl ether
PTZ: phenothiazine
THPIC: trishydroxypropyl isocyanurate
TDI: toluene diisocyanate IPDI: isophorone diisocyanate
HMDI: hexamethylene diisocyanate
HDDA: hexanediol diacrylate
TMPEOTA: trimethylolpropane oxyethylene triacrylate
TPGDA: tripropylene glycol diacrylate
AcOEt: ethyl acetate
Bu$_2$SnLau$_2$: dibutyltin dilaurate
ACN: acrylonitrile
NEMA: hydroxyalkylmethacrylamide
NEtz = triethylamine

EXAMPLES 1 TO 12

Preparation of a mixture of hydroxylated oligomers containing an isocyanurate nucleus by Michael addition of isocyanuric acid to 2-hydroxyethyl acrylate

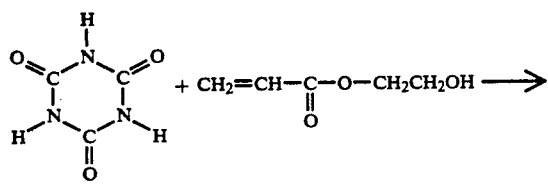

mixture of three compounds of general formula:

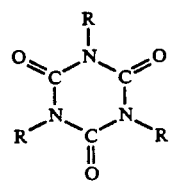

(1) one of the Rs denotes

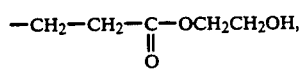

and the other two denote H (mono derivative);
(2) each of two Rs denotes

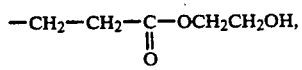

and and the other denotes H (di derivative); and
(3) the three Rs denote

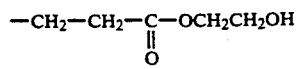

(tri derivative).

General operating method

Into a 1—1 reactor fitted with a central mechanical stirrer and a reflux condenser are introduced 375 ml of dimethyl formamide, 64.5 g (0.5 mol) of isocyanuric acid, a given quantity of catalyst (Triton B or TEBAC), 2000 ppm of HQME relative to isocyanuric acid and 1000 ppm of PTZ relative to isocyanuric acid.

The whole is heated to the temperature $T_1$, with air bubbling. A given quantity of hydroxyethyl acrylate is then introduced with the aid of a Gilson metering pump over a period $t_1$.

When the addition is finished, the temperature of the mixture is increased to $T_2$ and stirring is allowed to continue for a period $t_2$. The content of the reactor is then cooled and the latter is drained.

The catalyst is then neutralised with a 1N HCl solution and the reaction mixture, orangy-brown in colour, is then treated over active carbon (0.5% relative to the reaction mass; 80° C.; 1 hour), and is then filtered through Celite. Finally, the filtrate is concentrated in the rotary evaporator (60° C.; 400 Pa-3 mm Hg) to remove the dimethylformamide. An addition product consisting of a mixture of mono, di and tri derivatives is obtained.

The various operating conditions and the results obtained appear in Table 1 below. The mixtures obtained can be employed, without further purification, for the synthesis of urethano oligomers by reaction with a diisocyanate (NCO/OH ratio of 2), and then of urethanoacrylic oligomers by reaction of the latter with a hydroxyalkyl (meth)acrylate.

TABLE 1

| Ex | t$_1$ (h) | Catalyst | Molar ratio catalyst/AC | Molar ratio HEA/AC | T$_1$ (°C.) | T$_2$ (°C.) | t$_2$ (h) | Mono % | Di % | Tri % | HEA % | Mass g | R Mono | R Di | R Tri | ΣR % |
|----|-----------|----------|------------------------|--------------------|-----|-----|-----|-------|------|------|------|--------|--------|------|------|------|
| 1  | 1 | TriB  | 1.5  | 3.05 | 80 |     |     | 7.9  | 17.6 | 36.6 | >4.6 | 224.5 | 14.5 | 21.9 | 34.5 | 70.9 |
| 2  | 4 | "     | "    | 2.8  | 50 |     |     | 9.1  | 18.1 | 32.5 | >4.6 | 232   | 17.2 | 23.3 | 31.6 | 72.1 |
| 3  | 1 | TEBAC | "    | 2.8  | 80 |     |     | 11.9 | 13.3 | 14.6 | >4.6 | 210   | 20.4 | 15.5 | 12.9 | 48.8 |
| 4  | 4 | "     | "    | "    | 50 |     |     | 7.9  | 8.8  | 13.3 | 4.9  | 216   | 13.9 | 10.5 | 12.0 | 36.4 |
| 5* | 1 | TriB  | 3.1  | 3.05 | 50 |     |     | 7.7  | 17.7 | 35.1 | >4.6 | 412.8 | 13.0 | 20.2 | 30.4 | 63.6 |
| 6  | 4 | "     | "    | 2.8  | 80 | 156 | 1   | 6.2  | 18.3 | 44.5 | 3.9  | 219   | 11.0 | 22.2 | 40.9 | 74.2 |
| 7  | 1 | TEBAC | "    | "    | 50 |     |     | 10.2 | 11.0 | 16.9 | 7.2  | 210   | 17.5 | 12.8 | 15.3 | 45.6 |
| 8  | 4 | "     | "    | "    | 80 |     |     | 13.1 | 12.9 | 14.2 | 5.4  | 201   | 21.7 | 14.5 | 12.1 | 48.3 |
| 9  | 4 | TriB  | "    | "    | "  | 120 | 1   | 15.4 | 24.1 | 40.3 | 14.4 | 209.5 | 27.0 | 28.0 | 35.4 | 90.4 |
| 10 | 4 | "     | "    | "    | "  | "   | 0.5 | 17.2 | 24.3 | 41.8 | 16.1 | 208.2 | 29.3 | 28.0 | 36.5 | 93.8 |
| 11 | 4 | "     | "    | "    | "  | "   | 1   | 14.9 | 22.7 | 48.5 | 13.0 | 202.5 | 24.6 | 25.5 | 41.1 | 91.2 |
| 12 | 4 | "     | "    | "    | "  | "   | 1   | 25.8 | 25.0 | 29.5 | 1.2  | 165   | 34.8 | 22.9 | 20.4 | 78.1 |

*AC = 0.5 mole $R_{mono,\ di\ or\ tri} = \dfrac{\text{number of moles of mono- di or tri formed}}{\text{number of starting moles of Ac}} \times 100 \quad \Sigma R = R_{mono} + R_{di} + R_{tri}$

EXAMPLES 13 TO 21

(1) Preparation of an isocyanato urethano oligomer

Into a 250-ml reactor fitted with a central mechanical stirrer and a vertical condenser are introduced 30.3 g (0.1 mol) of THPIC powder, 82.5 g of anhydrous ethyl acetate and 52.2 g (0.3 mol) of TDI. The reaction mixture is then placed under dry nitrogen purging and the temperature is then brought to 60° C. over 3 hours, at the end of which time the degree of conversion of the NCO groups is close to 50%. The reaction mixture is then cooled to 30° C.

(2) Acrylation of the oligomer obtained in (1)

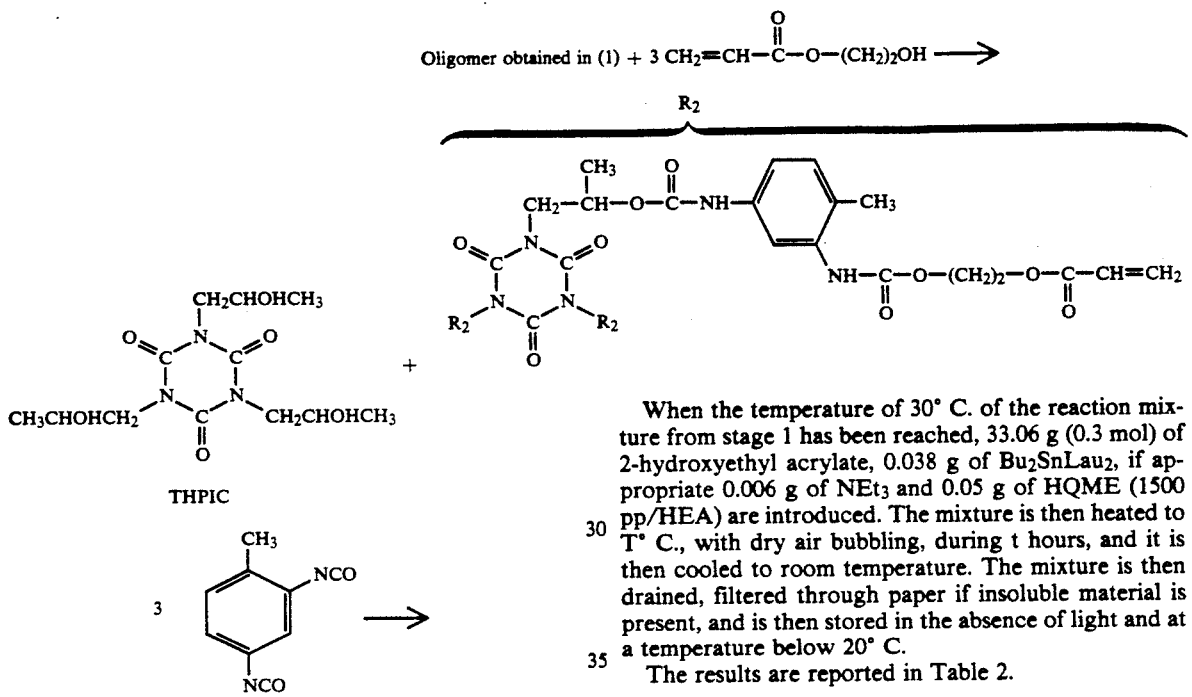

When the temperature of 30° C. of the reaction mixture from stage 1 has been reached, 33.06 g (0.3 mol) of 2-hydroxyethyl acrylate, 0.038 g of $Bu_2SnLau_2$, if appropriate 0.006 g of $NEt_3$ and 0.05 g of HQME (1500 pp/HEA) are introduced. The mixture is then heated to T° C., with dry air bubbling, during t hours, and it is then cooled to room temperature. The mixture is then drained, filtered through paper if insoluble material is present, and is then stored in the absence of light and at a temperature below 20° C.

The results are reported in Table 2.

TABLE 2

| Ex. | Solvent | SC (%)* | Catalyst | Molar ratio catalyst/oligomer obtained in (1) $10^{-4}$ | T (°C.) | t (h) | Mol NCO per 100 g $10^{-3}$ | DC NCO (%)** | % HEA | DC HEA (%)** | η(Pas) |
|---|---|---|---|---|---|---|---|---|---|---|---|
| 13 | HDDA | 25 | $Bu_2SnLau_2$ $NEt_3$ | 6 | 80 | 3 | 8.1 | 95.0 | 4.9 | 50 | 0.36 |
| 14 | AcOEt | 50 | $Bu_2SnLau_2$ $NEt_3$ | 3 | 100 | 6 | 1.1 | 99.6 | 9.4 | 46.9 | 17.2 |
| 15 | AcOEt | 25 | $Bu_2SnLau_2$ | 6 | 100 | 6 | 1.0 | 99.4 | 2.4 | 73.9 | 0.15 |
| 16 | HDDA | 25 | " | 3 | 80 | 6 | 7.9 | 99.5 | 5.3 | 45.8 | 0.30 |
| 17 | HDDA | 50 | " | 3 | 100 | 3 | 1.3 | 99.6 | 3.4 | 79.7 | 63*** |
| 18 | HDDA | 50 | $Bu_2SnLau_2$ $NEt_3$ | 6 | 80 | 3 | 4.8 | 98.4 | 5.4 | 67.6 | 2.5 |
| 19 | AcOEt | 50 | $Bu_2SnLau_2$ | 6 | 80 | 6 | 1.4 | 99.6 | 0.04 | 99.8 | 0.638 |
| 20 | AcOEt | 50 | " | 6 | 80 | 6 | 0.09 | 99.9 | 0.03 | 99.8 | 0.755 |
| 21 | AcOEt | 50 | " | 6 | 80 | 6 | 0.6 | 99.8 | 0.51 | 96.9 | 0.741 |

*SC = Solids content
**DC = Degree of conversion
***Limit of viscosity which can be measured with the apparatus

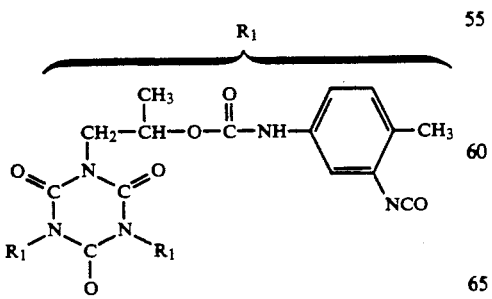

EXAMPLE 22

Various solutions of the urethano-acrylic oligomer obtained in stage 2 of Examples 19 to 21 in a number of multifunctional acrylates were produced at temperatures of 25° and 50° C. and the absolute viscosity was measured. The results are collated in Table 3.

TABLE 3

| Oligomer concentration | Reactive diluent | Viscosity (Pas) 25° C. | Viscosity (Pas) 50° C. |
|---|---|---|---|
| 25 | HDDA | 0.077 | 0.02 |

TABLE 3-continued

| Oligomer concentration | Reactive diluent | Viscosity (Pas) 25° C. | Viscosity (Pas) 50° C. |
|---|---|---|---|
| 50 | HDDA | 5 | 0.3 |
| 70 | HDDA | 399 | 9.7 |
| 25 | TMPEOTA | 1.3 | 0.15 |
| 50 | TMPEOTA | 21.5 | 2.1 |
| 70 | TMPEOTA | 10360 | 61.4 |
| 25 | TPGDA | 0.43 | 0.08 |
| 50 | TPGDA | 32.5 | .2 |
| 70 | TPGDA | 10360 | 169 |

EXAMPLES 23 TO 37

(a) Preparation of a THPIC+diisocyanate addition oligomer

Into a 250-cm³ reactor are introduced, at 20° C., 0.3 mol of diisocyanate, 0.1 mol of THPIC, an appropriate quantity of solvent to have a theoretical solids content of 50% and $3 \times 10^{-4}$ mol of Bu$_2$SnLau$_2$ per mole of THPIC in the case of IPDI and HMDI.

The content of the reactor is then heated to 60° C. with stirring for 2 hours, resulting in a percentage of residual isocyanate functional groups close to 50%.

The results are reported in Table 4.

TABLE 4

| Ex. | Solvent | Diisocyanate | Catalyst | NCO$_R$/NCO$_{in}$ To* | 1 h | 2 h | Theoretical oligomer mass (g) | η (Pas) |
|---|---|---|---|---|---|---|---|---|
| 23a | AcOEt | TDI | — | 96.2 | 65.3 | 56.9 | 825 | 0.019 |
| 24a | AcN | TDI | — | | 54.6 | 54.4 | 825 | — |
| 25a | AcOEt | HMDI | — | | 91.5 | 91.0 | 807 | — |
| 26a | AcOEt | HMDI | Bu$_2$SnLau$_2$ | | 45.7 | — | 807 | 0.033 |
| 27a | AcOEt | IPDI | — | | 100 | 100 | 969 | — |
| 28a | AcOEt | IPDI | Bu$_2$SnLau$_2$ | | 58.8 | 49.6 | 969 | 0.036 |

*T = 80° C.

(b) Reaction of the oligomer obtained in (a) with a hydroxylated acrylic derivative 0.1 Mol to 0.3 mol of hydroxylated acrylic derivative and 1000 ppm of HQME relative to the acrylic derivative are introduced at 20° C. into the above mixture and the contents of the reactor are heated to 60° C. for 2 hours (or more) to produce the desired degree of conversion. The results are reported in Table 5.

TABLE 5

| Ex. | Oligomer obtained in (a) | Acrylic Monomer | Molar ratio acrylic derivative/ ogligomer obtained in (a) | NCO$_R$/NCO$_{in}$* 1 h | 2 h | Final | Theoretical SC (%) | Theoretical oligomer mass (g) | η (Pas) |
|---|---|---|---|---|---|---|---|---|---|
| 23b | Ex 23a | HEMA | 2 | 28.9 | 21.3 | 16.1 | 56.8 | 1085 | 0.170 |
| 30b | Ex 23a | HEA | 2 | 18.2 | 14.6 | 14.6 | 56.5 | 1071 | 0.180 |
| 31b | Ex 23a | HPMA | 2 | — | 29.7 | 20.0 | 57.1 | 1099 | 0.44 |
| 32b | Ex 23a | HPA | 2 | 30.5 | 24.7 | 21.4 | 56.8 | 1083 | 0.09 |
| 33b | Ex 23a | NEMA | 2 | 29.2 | 26.4 | 19.1 | 56.8 | 1083 | 0.44 |
| 34b | Ex 23a | HEMA | 1 | 33.5 | 31.6 | 31.6 | 53.6 | 955 | 0.050 |
| 35b | Ex 23a | HEMA | 3 | 22.5 | 17.3 | 8.8 | 59.6 | 1215 | 0.280 |
| 36b | Ex 26a | HEMA | 2 | 13.3 | 12.8 | 12.8 | 56.9 | 1067 | 0.240 |
| 37b | Ex 28a | HEMA | 2 | 33.4 | — | 28.6 | 55.9 | 1229 | 0.007 |

*NCO$_R$NCO$_{in}$: resultant NCO/initial NCO
—: not determined solution in ethyl acetate is mixed with a reactive diluent. The solvent is then stripped off in the rotary evaporator (50° C.; $5.3 \times 10^3$ Pa) to give an (isocyanato)urethanoacrylic composition containing 30% by weight of starting oligomer.

The results are reported in Table 6.

TABLE 6

| Ex. | Oligomer | Reactive Diluent | Viscosity at 25° C. (Pas) | Number of mols of NCO per 100 g of solution |
|---|---|---|---|---|
| 38 | THPIC + TDI + 2HEA of Ex. | TMPEOTA | 2.51 | $8.5 \times 10^{-3}$ |
| 39 | THPIC + TDI + 2HEA of Ex. | TPGDA | 0.61 | $2.2 \times 10^{-2}$ |
| 40 | THPIC + TDI + 2HEA of Ex. | HDDA | 0.13 | $6 \times 10^{-2}$ |
| 41 | THPIC + IPDI + 2HEA of Ex. 37b | TMPEOTA | 1.33 | 0.66 |
| 42 | THPIC + TDI + 2HMPA of Ex. 31b | " | 2.72 | $5.5 \times 10^{-2}$ |
| 43 | THPIC + TDI + 2HPA of Ex. 32b | " | 1.74 | $5.6 \times 10^{-2}$ |
| 44 | THPIC + TDI + 2HEMA of Ex. 29b | " | 2.35 | $2.5 \times 10^{-2}$ |

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The entire disclosure of all applications, patents, and publications, cited above and below, and of corresponding French Application 90 08316, filed Jul. 2, 1990, are hereby incorporated by reference.

What is claimed is:

1. At least one oligomer containing isocyanurate units, of the formula:

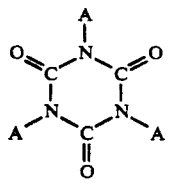

wherein:
(1) at least one A' residue is of the formula (a):

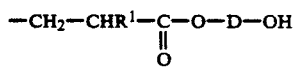 (a)

wherein $R^1$=H or $CH_3$ and D=$C_1$-$C_4$ alkylene, residue, any remaining A residues denote H or $C_1$-$C_4$ alkyl, and optionally at least a part of the A residues of the formula (a) represent

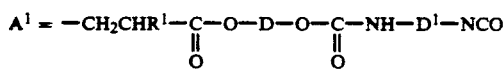

wherein $D^1$ is a divalent organic radical free from groups which react with isocyanate groups and is obtained by elimination of 2 NCO groups from a polyisocyanate, or at least a part of the $A^1$ residues represent groups $A^2 =$

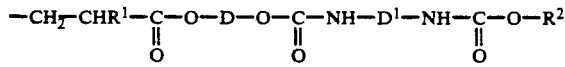

wherein $R^2$ is a monovalent radical obtained by elimination of the hydroxyl group from a monoalcohol containing a vinylidene group, and free from other groups which react with isocyanate groups; or
(2) at least one A residue denotes:

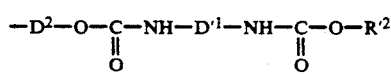 (b)

wherein
$D^2$ is a a residue —$D^3$—(—O—$D^3$—)$_n$— wherein $D^3$ is a $C_1$-$C_4$ alkylene residue optionally substituted by halogen, and n is an integer from 1 to 12;
$D'^1$ is $D^1$ defined above;
$R'^2$ is $R^2$ defined above, and
any remaining A residue(s) denote

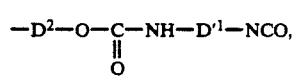

$D^2$ and $D'^1$ being as defined above.

2. An oligomer according to claim 1, wherein $R^2$ or $R'^2$ are denoted by:

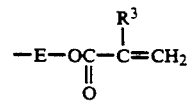

where:
$R^3$ denotes H or $CH_3$; and
E denotes a unit

x being an integer from 1 to 12, and $R^4$ and $R^5$, which are identical or different, represent hydrogen or and alkyl containing 1 to 4 carbon atoms.

3. A mixture of oligomers according to claim 2, wherein the oligomers are in a dilute state in a multifunctional acrylate in an oligomer/multifunctional acrylate ratio of 20–80% by weight.

4. An oligomer according to claim 2, wherein $R^2$ or $R'^2$ originates from at least one out of hydroxypropyl (meth)acrylate, hydroxyethyl (meth)acrylate and their mixtures.

5. A mixture of oligomers according to claim 4, wherein the oligomers are in a dilute state in a multifunctional acrylate in an oligomer/multifunctional acrylate ratio of 20–80% by weight.

6. An oligomer according to claim 1, wherein $R^2$ or $R'^2$ represent

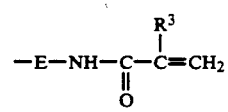

wherein E denotes a unit

x being an integer from 1 to 12, and $R^4$ and $R^5$, which are identical or different, represent a hydrogen atom or an; alkyl radical containing 1 to 4 carbon atoms.

7. A mixture of oligomers according to claim 6, wherein the oligomers are in a dilute state in a multifunctional acrylate in an oligomer/multifunctional acrylate ratio of 20–80% by weight.

8. A mixture of oligomers according to claim 1, in the dilute state in a multifunctional acrylate, in an oligomer/multifunctional acrylate ratio of 20 to 80% by weight.

9. (Amended.) A process for the preparation of the oligomers as defined in (1) of claim 1, wherein
in a first stage a Michael reaction is carried out between a compound of formula

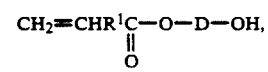

$R^1$ and D being as defined in claim 1, and isocyanuric acid, with a basic catalyst and in a solvent medium, to obtain at least one oligomer;

in a second stage, a urethanization is carried out by reacting the oligomer(s) obtained with a polyisocyanate OCN—$D^1$—NCO, $D^1$ being as defined in claim 1; and in a third stage, a reaction of the product from the preceding stage is carried out with a monoalcohol $R^2$OH, $R^2$ being as defined in claim 1;

then, optionally, the solvent is removed.

10. A process according to claim 9, wherein the Michael reaction is carried out by reacting the compound of formula

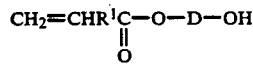

and isocyanuric acid at a temperature of 60°-100° C. over a period of 1-4 hours, heating at a temperature of 110°-156° C. is then carried out for 0.1-2 hours, the catalyst is then neutralised and the purification stage is carried out.

11. A process according to claim 10, wherein a mixture of the oligomers obtained are mixed with a multifunctional acrylate in an oligomer/multifunctional acrylate ratio of 20-80% by weight.

12. A process according to claim 9, wherein the oligomers obtained are mixed with a multifunctional acrylate in an oligomer/multifunctional acrylate ratio of 20 to 80% by weight.

13. A mixture of three oligomers according to claim 1 of the formula

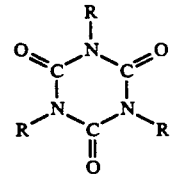

wherein
(a) one of the R groups denotes

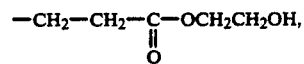

and the other two denote H;
(b) each of the two R groups denotes

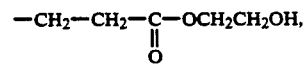

and the other denotes H; and
(c) the three R groups denote

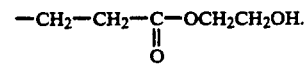

14. A (co)polymer including at least one unit derived from at least one oligomer containing an isocyanurate unit according to claim 1.

15. At least one oligomer according to claim 1, wherein in said oligomer at least one A residue denotes a residue of formula (a).

16. At least one oligomer according to claim 1, wherein in said oligomer at least one A residue denotes a residue of formula (b).

17. At least one oligomer according to claim 16, wherein the oligomer carries less than 3 (b) groups.

18. An oligomer according to claim 16, wherein $D^2$ is a $C_1$-$C_4$ alkylene residue substituted by halogen; or a residue —$D^3$—(—O—$D^3$—)$_n$— wherein $D^3$ is a $C_1$-$C_4$ alkylene residue optionally substituted by halogen, and n is an integer from 1 to 12.

19. An oligomer according to claim 16, wherein $D^2$ is a residue —$D^3$—(—O—$D^3$—)$_n$— wherein $D^3$ is a $C_1$-$C_4$ alkylene residue optionally substituted by halogen, and n is an integer from 1 to 12.

* * * * *

UNITED STATES PATENT AND TRADEMARK OFFICE
CERTIFICATE OF CORRECTION

PATENT NO. : 5,256,748
DATED : October 26, 1993
INVENTOR(S) : Didier VANHOYE et al.

It is certified that error appears in the above-identified patent and that said Letters Patent is hereby corrected as shown below:

Title page, item,

(73) Assignee: Please change "Autochem" to read:

-- ATOCHEM --

Signed and Sealed this

Seventh Day of June, 1994

Attest:

BRUCE LEHMAN

Attesting Officer

Commissioner of Patents and Trademarks